United States Patent
Ueberall

(10) Patent No.: US 8,246,839 B2
(45) Date of Patent: *Aug. 21, 2012

(54) DOUBLE-WALLED CHAMBER FOR ULTRA VIOLET RADIATION TREATMENT OF LIQUIDS

(75) Inventor: Peter Ueberall, Uetersen (DE)

(73) Assignee: Trojan Technologies Inc. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/752,965

(22) Filed: Apr. 1, 2010

(65) Prior Publication Data

US 2010/0187437 A1  Jul. 29, 2010

Related U.S. Application Data

(63) Continuation of application No. 10/514,042, filed as application No. PCT/CA03/00656 on May 9, 2003, now Pat. No. 7,691,343.

(30) Foreign Application Priority Data

May 10, 2002 (DE) .................................. 102 21 037

(51) Int. Cl.
    *C02F 1/32* (2006.01)
(52) U.S. Cl. .................... 210/748.1; 422/186.3; 422/20; 422/24; 210/748.01; 210/748.11; 250/432 R; 250/436
(58) Field of Classification Search .. 210/748.01–748.1, 210/739, 600; 422/186.3, 20, 22, 24, 186, 422/186.1; 250/554, 435, 436, 432 R, 455.11; 204/554; 426/235; 96/224
    See application file for complete search history.

(56) References Cited

U.S. PATENT DOCUMENTS

| | | | | |
|---|---|---|---|---|
| 2,935,611 A | * | 5/1960 | Myers | 250/435 |
| 3,551,091 A | * | 12/1970 | Veloz | 210/251 |
| 4,857,204 A | | 8/1989 | Joklik | |
| 5,352,359 A | * | 10/1994 | Nagai et al. | 210/192 |
| 5,573,666 A | * | 11/1996 | Korin | 210/232 |
| 5,597,482 A | * | 1/1997 | Melyon | 210/209 |
| 6,099,799 A | * | 8/2000 | Anderson | 210/748.11 |
| 6,283,159 B1 | * | 9/2001 | Tada | 138/116 |

(Continued)

FOREIGN PATENT DOCUMENTS

FR 2545473 A 11/1984

(Continued)

OTHER PUBLICATIONS

Mar. 11, 2010 Canadian Office Action for Canadian Patent Application No. 2,484,849.

Apr. 19, 2006 letter from Wilkinson & Grist providing a detailed description of the First Office Action for Chinese Patent Application No. 03810493.8.

(Continued)

*Primary Examiner* — Joseph Drodge
*Assistant Examiner* — Cameron J Allen
(74) *Attorney, Agent, or Firm* — Katten Muchin Rosenman LLP

(57) ABSTRACT

The object of the invention is a double-walled chamber for the UV disinfection of liquids, preferably drinking water and/or waste water. It realizes a rectangular and/or square cross-sectional shape of the UV radiation chamber even at higher pressures, whereby the radiation chamber can moreover be provided with a thin-walled configuration and allows an optimal and close arrangement of UV radiators as compared with a round chamber. By applying the inventive idea, the known dead zones at the entrance are completely eliminated and an entrance turbulence is produced which runs simultaneously with the piston flow in the chamber.

16 Claims, 2 Drawing Sheets

U.S. PATENT DOCUMENTS

| | | | |
|---|---|---|---|
| 7,687,785 B2 * | 3/2010 | Chen | 250/436 |
| 7,691,343 B2 * | 4/2010 | Ueberall | 422/186.3 |
| 2002/0043504 A1 * | 4/2002 | Chen et al. | 210/748 |

FOREIGN PATENT DOCUMENTS

| | | | |
|---|---|---|---|
| JP | 2001212214 A | * | 8/2001 |
| KR | 2010003488 A | * | 1/2010 |

OTHER PUBLICATIONS

Apr. 19, 2007 letter from Wilkinson & Grist providing a detailed description of the Second Office Action for Chinese Patent Application No. 03810493.8 and the Office Action.

Nov. 26, 2010 Office Action for European Patent Application No. 03 724 700.4.

* cited by examiner

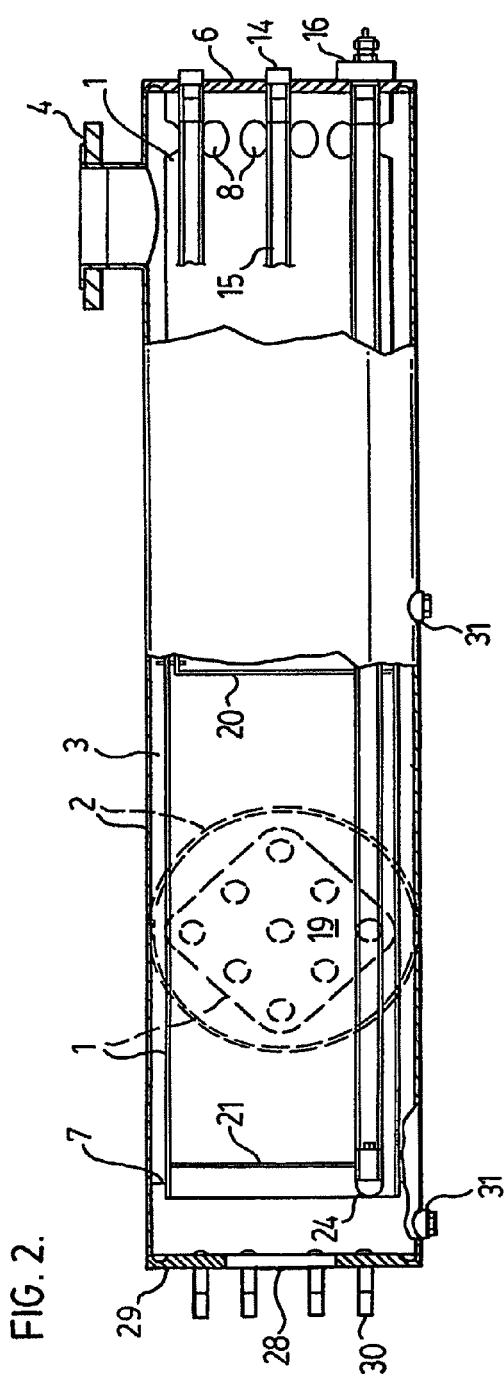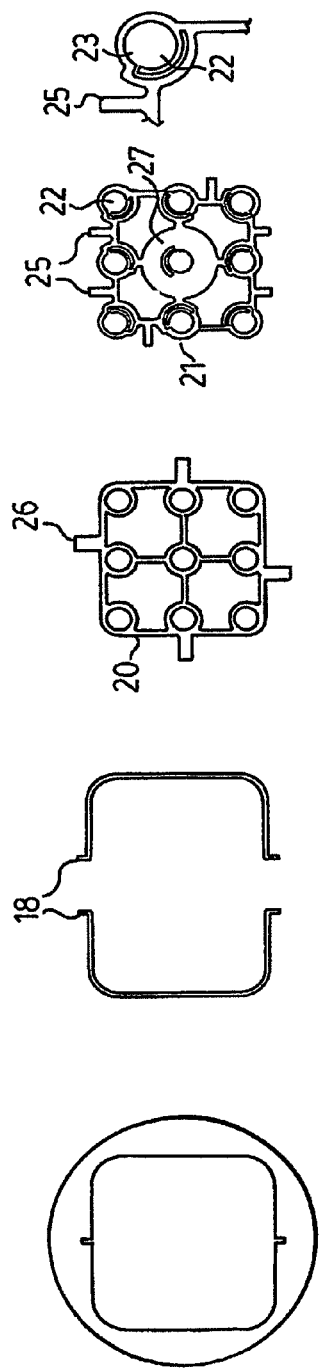

DOUBLE-WALLED CHAMBER FOR ULTRA VIOLET RADIATION TREATMENT OF LIQUIDS

This application is a continuation of U.S. patent application Ser. No. 10/514,042 now U.S. Pat. No. 7,691,343, filed Jul. 1, 2005, which is a 371 of International Appln. No. PCT/CA03/00656, filed May 9, 2003, which claims the benefit of German Appln. No. 102 21 037.3, filed May 10, 2002, the contents of all incorporated herein by reference.

FIELD OF THE INVENTION

In one of its aspects, the present invention relates to a double-walled chamber, particularly such a chamber suitable use in the ultraviolet (UV) treatment or disinfection of liquids, preferably drinking water and/or wastewater.

DESCRIPTION OF THE PRIOR ART

UV radiation chambers are usually round boiler-like vessels through which the medium to be treated flows axially. Typically, a conventional UV radiation chamber is provided with inlet and outlet connections laterally at the end, partly also with axially directed outlets. It is conventional that the inlet and outlet connections, like other pressure vessels, are manufactured from round pipes, typically standardized special steel pipes.

The pipe connections and/or the round boiler-like chamber or vessel tolerate high internal pressures at a use of minimal material. The circular shape of the boiler-like chamber or vessel is the optimal solution. In such a round vessel there are disposed the radiation devices which emit radiation, preferably for disinfection of the fluid medium being treated. These are configurations (arrays) of UV radiation devices which are inserted into a UV-permeable thin-walled quartz tubes for protection against low temperature and humidity. With a few exceptions, the UV radiation devices are disposed longitudinally in the tube-like UV radiation chambers, meaning that they are arranged such that their longitudinal axis is substantially parallel to the direction of fluid flow through the chamber or vessel.

It is normally the goal of the designer to produce the most homogeneous UV radiation field with approximately the same intensity of radiation at each place within the chamber. Thus, the goal is to treat the liquid molecules or "particles" such that they are disinfected in their entirety and each molecule or "particle" individually is subjected to the same radiation "H" ($mJ/cm^2$; $J/m^2$).

In a hydraulic system, the cross-flow of the radiation chamber should occur, if possible, in the form of a piston flow (plug flow) along the chamber axis with an overlap by many co-running inner transversal flow components, i.e., radial side flow movements. Only in this way will the individual liquid molecules or "particles" move again to the direct vicinity of the quartz cladding tubes in which the UV radiators are situated and where there is a high radiation intensity and the destruction of germs or microorganisms occurs nearly directly. Such a flow behavior enhances the disinfection performance of the UV treatment device.

The classical ideal and laminar flow pattern is therefore not desirable. It has been noticed, however, that such a flow pattern can be achieved more easily from a technical viewpoint than the truly "ideal" flow for an effective UV de-germination, which depends predominantly on the design of the chamber and the inlet and outlet conditions of the same. The occurrence of dead zones by the lateral entrance of the medium into the cylindrical radiation chamber which are caused by too fast and uncontrollable deflection of the incoming liquid stream and a lack of inner radial movement components often prevent the utilization of the theoretically available radiation space (radiation duration) in the cylindrical radiation chambers.

An additional factor is that the UV radiation sources or lamps disposed along the chamber cannot be conveniently arranged in a circular pattern such that one can refer to a homogeneous radiation field over the cross section and thus in the entire chamber volume. Typically, homogeneous radiation fields are only achieved with even rectangular grid arrays of radiation sources or lamps which demand a rectangular, and preferably square flow cross section. Unfortunately, such an arrangement becomes problematic, however, when a considerable pressure prevails in the interior of the chambers, which is nearly always the case in the treatment of drinking water.

In summary, it can be said that the usual cylindrical UV radiation chambers with the lateral inlets and axially parallel UV radiator arrangements show three special deficiencies, namely: (i) that dead spaces are produced, (i) that a bunch of radiation sources or lamps cannot be conveniently arranged evenly in a round or circular cross section, and (iii) that the passing main flow is not overlapped by a sufficient number of radial side flows.

Thus, there remains a need in the art for a chamber, vessel or treatment device which obviates or mitigates at least one of the above-mention disadvantages of the prior art, particularly such a chamber, vessel or treatment device for UV irradiation of fluid such was wastewater, drinking water and the like.

SUMMARY OF THE INVENTION

It is an object of the present invention to provide a novel chamber, vessel or treatment device of obviates or mitigates at least one of the above-mentioned disadvantages of the prior art.

According in one of its aspects, the present invention provides a double-walled chamber for the UV disinfection of liquids comprising: (i) an inlet connection; (ii) an outlet connection; (iii) an outer pipe which encloses an inner pipe in which at least on UV radiation source is disposed and at whose ends there is a sealing cover in which there can also be an outlet and/or inlet opening, characterized in that the entrance of the liquid into the inner pipe with the radiation devices occurs through the intermediate space between the outer and inner pipe.

BRIEF DESCRIPTION OF THE DRAWINGS

Embodiments of the present invention will be described with reference to the accompanying drawings, wherein like reference numerals denote like parts, and in which:

FIG. 1b is a sectional view along line AB in FIG. 1a;

FIGS. 2, 2a, 2b, 2c and 2d illustrate a second preferred embodiment of the present invention.

DETAILED DESCRIPTION OF THE PREFERRED EMBODIMENTS

Figure 1A:
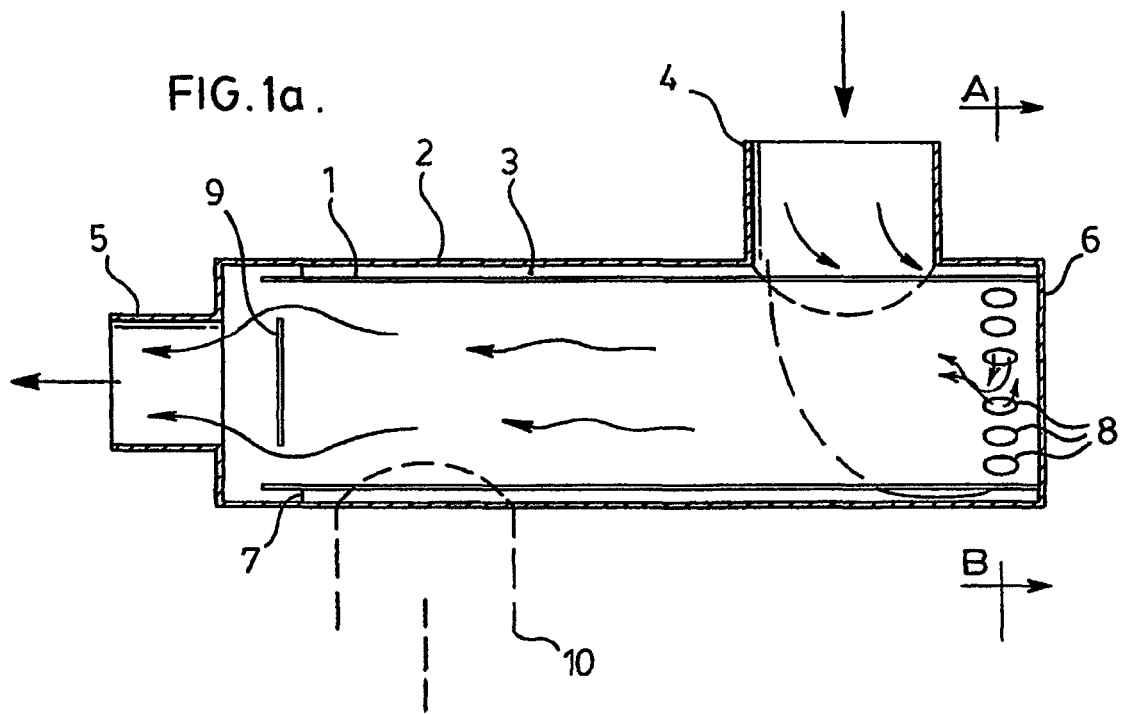
FIG. 1a illustrates a first preferred embodiment of the present invention.
Figure 1B:
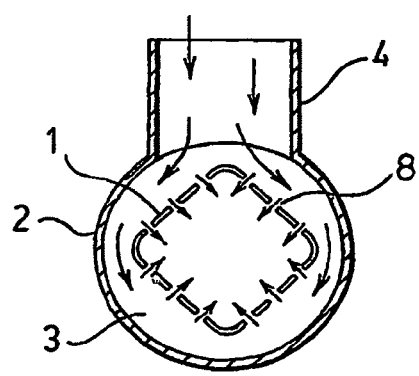

Thus, a preferred embodiment of the present invention is illustrated in FIGS. 1a and 1b, in which, for clarity, the UV radiation devices, i.e. the UV radiation sources or lamps with the cladding tubes and the radiation source or lamp hatches, are not shown. Instead, there is illustrated only the double chamber with the guidance of the passing medium.

With reference to FIGS. 1a and 1b, reference numeral 1 relates to the thin-walled inner pipe of any random cross-section, e.g., a square cross section, in which the UV radiation source or lamp configuration is disposed. Reference numeral 2 relates an outer pressure-tight round pipe with an inlet nozzle 4 and an outlet nozzle 5. Reference numeral 3 relates to the intermediate space between the two pipes 1 and 2.

The inner pipe 1 is tightly connected with the round floor 6, e.g., by welding on the face surface at the outlet end of the chamber and centering by means of the adapted separating wall 7 at the end side. The inner pipe 1, which is the actual radiation chamber with the radiation devices (again not shown for clarity), is provided at its inlet end with a circular ring of round inlet openings 8 and the baffle plate 9 at the outlet end.

According to this preferred embodiment of the invention, the liquid medium reaches from the inlet nozzle 4 at first into the intermediate space 3 and from there by the circularly arranged inlet openings the inner pipe 1, which is the actual radiation chamber. Since virtually the same pressure prevails in the intermediate space 3 and in the inner pipe 1, the inner pipe 1 can be produced irrespective of its shape of thin-walled sheet metal, which facilitates production considerably.

The outer pipe 2 is a round pipe which can be pressurized from the inside and can be produced from a relatively thin-walled material. As is shown particularly in FIG. 1b, the medium revolves about the inner pipe of square cross section, reaches under virtually the same pressure the conforming inlet openings 8 and passes through the same in separated partial streams with nearly the same injection speed peripherally into the inner pipe 1. The partial streams meet one another and mix with each other. It is easy to see that in this way turbulence and transverse movement of the fluid is obtained when the partial streams meet each other and that a dead space cannot occur at the inlet.

Notice should further be taken that the liquid flow will yield at the narrow places 9 in the axial direction and that thus the "channel cross section" will expand. It is irrelevant where precisely the inlet nozzle is located on the outer pipe. As is shown with the broken line, it could also be attached at reference numeral 10 from below. This may be of relevance when retrofitting a device, because in this way only a short piece needs to be opened for retrofitting the device when the inlet nozzle and the outlet nozzle are close to one another. One advantage in the arrangement of the inlet nozzle at reference numeral 10 is also that the intermediate space 3 is also continuously flushed.

Thus, some of the advantages of this preferred embodiment of the invention include:
1. A non-round, e.g. square, cross section of the actual UV radiation chamber for an optimal radiator configuration; chamber with a thin-walled housing.
2. Prevention of dead spaces in the inflow region.
3. An outstanding swirling of the medium after the entrance into the UV radiation chamber which is entrained by the main flow.

With reference to FIG. 2, there is illustrate another embodiment of the present invention.

Thus, FIG. 2 illustrates a double-walled chamber according a preferred embodiment of the present invention an exemplary technical arrangement in a slightly simplified representation. Preferably the material of choice is stainless steel in all parts.

Reference numeral 1 relates to the inner thin-walled pipe with a square cross section, i.e., the actual UV radiation chamber, reference numeral 2 relates to the outer pressure-tight and round pipe and reference numeral 3 to the intermediate space between the two pipes. The wall thickness preferably is about 1.5 mm for the inner pipe and about 3 mm for the outer round pipe. The diameter of the outer pipe is approx. 320 mm. The cross sections and the arrangement of the cladding tubes 19 are shown in broken lines.

Reference numeral 4 relates to the inlet nozzle, which is arranged as a loose rotating flange. Reference numeral 6 relates to the front floor with lead-throughs of the cladding tubes 14 into which the UV radiation sources or lamps 15 are inserted. Reference numeral 16 relates to the press rings with a radiator cable screw connections 17 with O-rings which rest flat on the floor and which seal the cladding tubes 14 in a pressured substantially water-tight manner to the outside.

The discharge of the irradiated water occurs via a central flange connection 28 with the welded stud bolts 30 in the rear chamber floor 29. The inner pipe 1, which represents the actual UV radiation chamber, is provided at the inlet end with the inlet openings 8 which are arranged in a ring-like way and is welded on the inner side of the floor all around in a sealed manner to the same. The inlet nozzle 4 is slightly offset to the rear, so that the incoming liquid cannot flow more strongly into the upper inlet openings.

At the outlet end of the double-wall chamber, the inner square pipe is fitted into the separating wall 7, which is a laser cutting with a plate thickness of 1.5 mm, and welded to the same. The shape of the separating wall 7 is shown by FIG. 2a. The inner pipe itself consists of two lasered 1.5 mm plate halves which are canted with a defined radius and are to be welded together at an intended narrow bordering 18.

The configuration 19 shown in FIG. 2 in a sectional view of the nine provided UV low-pressure radiation sources or lamps has been used in the construction in a consistent and aligned manner: starting from floor 6, in the collecting shield 20 according to FIG. 2c and in the flow screen 21 according to FIG. 2d. The cladding tubes 14 are inserted and held in the flow screen 21 and a baffle plate 27 is also lasered into the same. The middle radiator holder 20 has the task of receiving the cladding tubes during the installation and preventing the same from dropping and breaking.

Once the cladding tubes have been inserted into the middle radiator holder 20, they will always find their fixing device in the flow screen 21 when they are pushed in further. Components 20 and 21 are also laser cuts. They can be produced easily, precisely and cheaply. The important aspect is, which needs to be mentioned specifically, that the mounting of the cladding tubes in the flow screen is made free from play so that they cannot vibrate, which could lead to destruction thereof.

The openings 22 in the flow screen 21 according to FIG. 2d comprise bending clips 23 which can be bent out to such an extent that the cladding tubes can latch in with the round end 24 practically free from play during the insertion and will thus sit tightly. The welding of the flow screen 21 occurs by turning the welding clips 25 by 90°, whereupon one can weld them at both sides with a weld in the tube and can thus prevent crevice corrosion. In the case of the middle radiator holder 20, the clips 26 are bent by 90°, a bolt each is welded on to the same, which bolt latches into the provided hole when in position and is welded on consistently from the outside with an HV weld in order to prevent crevice corrosion in this manner. The openings 31 are used for emptying.

With the nine low-pressure radiators with an output of 230 W and a 253.7 nm radiation flux of 80 W one can still disinfect approx. 60 m3/h of cleared and pre-filtered waste water with a transmission of only 0.55% by 1 cm according to EU directives for bathing water.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A double-walled chamber for the UV disinfection of liquids comprising:
    an inlet connection;
    an outlet connection;
    an outer pipe having a circular cross-section;
    an inner pipe having a substantially rectangular cross section in which at least one UV radiation source is disposed and having a sealing cover in at least one end thereof, a downstream end of said outer pipe enclosing a downstream end of said inner pipe, the cross sectional shape of the outer pipe and the cross sectional shape of the inner pipe differing from one another, wherein the entrance of the liquid into the inner pipe with the radiation devices occurs through an intermediate space defined between the outer pipe and the inner pipe, the inner pipe completely enclosed by said outer pipe, said inner pipe having a non-circular cross-section and configured to hold a plurality of UV radiation sources therein disposed in an array substantially corresponding to the inner pipe non-circular cross-section, ends of the radiation sources being sealed exteriorly of said inner pipe;
    a plurality of inlet openings disposed at an end of said inner pipe and configured to cause (i) liquid flowing through said inlet connection to flow through the intermediate space before entering said plurality of inlet openings, and (ii) radial side flow movement of the liquid substantially through said inner pipe; and
    the intermediate space being configured to retain the liquid therein except for the liquid flowing through the plurality of openings.

2. The double-walled chamber defined in claim 1, wherein a thickness of the inner pipe is less than a thickness of the outer pipe.

3. The double-walled chamber defined in claim 1, wherein the outer pipe comprises a pressure vessel, and wherein the inner pipe is not a pressure vessel.

4. The double-walled chamber defined in claim 1, wherein the inner pipe has a substantially square cross-section.

5. The double-walled chamber defined in claim 1, wherein at the inner pipe is configured to hold an array of four or more UV radiation sources.

6. The double-walled chamber defined in claim 1, further comprising a baffle disposed inside the another end of the inner pipe.

7. An ultraviolet radiation fluid disinfection device comprising:
    a fluid inlet;
    a fluid outlet;
    a fluid treatment zone disposed between the fluid inlet and the fluid outlet, the fluid treatment zone comprising a first conduit portion having a substantially circular cross section completely enclosing a second conduit portion whereby a downstream end of the first conduit portion extends further in the downstream direction than a downstream end of the second conduit portion, the second conduit portion has a substantially rectangular cross section wherein the second conduit portion has a rectangular cross-sectional shape, wherein at least four UV radiation sources are disposed in a rectangular array within the second conduit portion having a cross-section which substantially corresponds to the cross-section of said second conduit portion, the cross-sectional shape of the first conduit portion and the cross-sectional shape of the second conduit portion differing from one another to define a fluid flow region in fluid communication with an interior of the second conduit portion through a plurality of openings disposed at an end of said second conduit portion, the plurality of openings and the cross-section of the second conduit portion being configured (i) to cause turbulence inside the second conduit portion so that fluid flow inside the second conduit portion is substantially free of dead spaces, and (ii) to promote swirling of fluid in the interior of the second conduit portion.

8. The fluid treatment system defined in claim 7, wherein the first conduit portion has a thicker wall than the second conduit portion.

9. The fluid treatment system defined in claim 7, wherein the second conduit portion does comprises a non-circular cross-section.

10. The fluid treatment system defined in claim 7, wherein the first conduit portion and the second conduit portion are in a coaxial arrangement.

11. An ultraviolet liquid treatment apparatus, comprising:
    a cylindrically-shaped outer pressure vessel having a liquid inlet, a liquid outlet, and an outer wall having a thickness;
    a radiation chamber disposed inside of said outer pressure vessel and having a non- circular cross-section which defines an intermediate liquid flow area between said radiation chamber and said outer pressure vessel, said radiation chamber having an outer wall having a thickness which is less than the thickness of the outer pressure vessel wall, said radiation chamber having a plurality of openings in an end thereof configured to receive liquid from said intermediate liquid flow area and provide radial side flow movement of the liquid inside said radiation chamber, said radiation chamber having a liquid outlet;
    a separating structure configured to direct the liquid to flow toward the plurality of openings, the separating structure disposed between said outer pressure vessel and said radiation chamber toward respective downstream ends thereof, and configured to retain liquid in the intermediate space, said separating structure having an outer shape which is different from an inner shape;
    a plurality of UV radiation sources disposed in an array inside said radiation chamber and configured to irradiate the liquid inside said radiation chamber; and
    said intermediate liquid flow area being configured to permit liquid to exit therefrom only through said plurality of openings in said radiation chamber.

12. Apparatus according to claim 11, wherein said radiation chamber is disposed entirely within said outer pressure vessel.

13. Apparatus according to claim 11, further comprising a baffle disposed at another end of the radiation chamber and configured to provide swirl of liquid flowing inside the radiation chamber.

14. Apparatus according to claim 11, wherein said radiation chamber has a substantially square cross-section, and wherein said plurality of UV radiation sources are disposed in an array have a substantially square cross-section configured to substantially match the square cross-section of said radiation chamber.

15. Apparatus according to claim 14, wherein said liquid inlet is disposed with a longitudinal axis thereof substantially perpendicular to a longitudinal axis of said outer pressure vessel.

16. Apparatus according to claim 15, wherein the longitudinal axis of the liquid inlet is disposed to substantially bisect a corner of the square cross-section radiation chamber.

* * * * *